(12) United States Patent
Bonzani, Jr.

(10) Patent No.: US 12,098,859 B2
(45) Date of Patent: Sep. 24, 2024

(54) FEEDBACK-DRIVEN AIR TREATMENT SYSTEM FOR NEW AND EXISTING BUILDINGS

(71) Applicant: AirPure Control Systems, LLC, Manchester, CT (US)

(72) Inventor: Peter J. Bonzani, Jr., Bolton, CT (US)

(73) Assignee: AirPure Control Systems, LLC, Manchester, CT (US)

(*) Notice: Subject to any disclaimer, the term of this patent is extended or adjusted under 35 U.S.C. 154(b) by 395 days.

(21) Appl. No.: 17/456,829

(22) Filed: Nov. 29, 2021

(65) Prior Publication Data

US 2022/0170661 A1    Jun. 2, 2022

Related U.S. Application Data (60) Provisional application No. 63/119,798, filed on Dec. 1, 2020.

(51) Int. Cl.
| | |
|---|---|
| *B01D 46/00* | (2022.01) |
| *A61L 9/20* | (2006.01) |
| *B01D 46/42* | (2006.01) |
| *B01D 46/46* | (2006.01) |
| *B03C 3/011* | (2006.01) |
| *F24F 8/108* | (2021.01) |
| *F24F 8/22* | (2021.01) |
| *F24F 8/30* | (2021.01) |
| *F24F 11/74* | (2018.01) |
| *F24F 13/08* | (2006.01) |
| *F24F 110/65* | (2018.01) |
| *F24F 110/70* | (2018.01) |

(52) U.S. Cl.
CPC ............... *F24F 11/74* (2018.01); *A61L 9/20* (2013.01); *B01D 46/0028* (2013.01); *B01D 46/429* (2013.01); *B01D 46/46* (2013.01); *B03C 3/011* (2013.01); *F24F 8/108* (2021.01); *F24F 8/22* (2021.01); *F24F 8/30* (2021.01); *A61L 2209/11* (2013.01); *A61L 2209/12* (2013.01); *A61L 2209/14* (2013.01); *B01D 2279/50* (2013.01); *B01D 2279/65* (2013.01); *B03C 2201/24* (2013.01); *F24F 2013/088* (2013.01); *F24F 2110/65* (2018.01); *F24F 2110/70* (2018.01)

(58) Field of Classification Search
CPC .. B01D 46/0028; B01D 46/429; B01D 46/46; B01D 2279/14; B01D 2279/65; F24F 11/74; F24F 8/22; F24F 8/30; F24F 2013/088; F24F 2110/70; B03C 3/38
USPC .............. 55/385.2, 385.1, DIG. 34; 454/187; 422/121, 186.04, 186.3
See application file for complete search history.

(56) References Cited

U.S. PATENT DOCUMENTS

| | | | | |
|---|---|---|---|---|
| 5,424,806 | A | * | 6/1995 | Siegel ............... H05K 7/20009 399/92 |
| 5,607,647 | A | * | 3/1997 | Kinkead ............... A61L 9/046 422/177 |
| 6,132,309 | A | * | 10/2000 | Panelli ................. F24F 3/167 55/385.2 |

(Continued)

*Primary Examiner* — Minh Chau T Pham
(74) *Attorney, Agent, or Firm* — Duane Morris LLP (57) ABSTRACT

An air treatment system includes an air handling unit to direct air into a building structure; a sensor to detect the presence of a target material and produce a signal indicative of the detection of a target material greater than a threshold amount; and a control system to control the air handler based on the signal from the sensor.

20 Claims, 11 Drawing Sheets

(56) References Cited

U.S. PATENT DOCUMENTS

| | | | |
|---|---|---|---|
| 8,747,753 B2* | 6/2014 | Engel | H05B 41/3922 |
| | | | 422/119 |
| 9,702,577 B1* | 7/2017 | Lachapelle | F24F 11/77 |
| 10,507,422 B2* | 12/2019 | Combs | B01D 46/429 |
| 11,717,783 B2* | 8/2023 | Landy | B01D 46/0049 |
| | | | 96/223 |
| 2007/0180801 A1* | 8/2007 | Paterson | F24F 8/192 |
| | | | 55/471 |
| 2008/0041025 A1* | 2/2008 | Boyer | F24F 1/035 |
| | | | 55/290 |
| 2010/0035537 A1* | 2/2010 | Ho | F24F 8/80 |
| | | | 55/327 |
| 2013/0086876 A1* | 4/2013 | Ikeda | G01N 15/0255 |
| | | | 55/418 |
| 2014/0020561 A1* | 1/2014 | Aery | B01D 46/60 |
| | | | 55/467 |
| 2014/0260131 A1* | 9/2014 | Burkhauser | A01G 9/246 |
| | | | 55/385.2 |
| 2020/0132324 A1* | 4/2020 | Rigg | F24F 11/72 |
| 2020/0141608 A1* | 5/2020 | Sinha | F24F 11/74 |
| 2023/0119976 A1* | 4/2023 | Maletich | F24F 8/158 |
| | | | 55/307 |
| 2023/0167987 A1* | 6/2023 | Kjellman | F24F 9/00 |
| | | | 55/385.2 |

\* cited by examiner

FEEDBACK-DRIVEN AIR TREATMENT SYSTEM FOR NEW AND EXISTING BUILDINGS

CROSS REFERENCE TO RELATED APPLICATIONS

This application claims the benefit of U.S. Provisional Patent Application No. 63/119,798, filed on Dec. 1, 2020, which is hereby incorporated by reference for all purposes as if fully set forth herein.

TECHNICAL FIELD

The present disclosure relates to an air treatment system for new and existing buildings and other structures, and more particularly, to a feedback-driven air treatment system that reduces and/or eliminates microbial agents in conditioned spaces, including, for example, an air quality management system to assist commercial and municipal structures in collecting, removing and neutralizing harmful pathogens.

BACKGROUND

Due to the COVID-19/SARS-CoV-2 pandemic, it has become paramount to reduce viral load in structures, particularly commercial and government buildings. Significant loss of life, economic damage and national security issues are weighing heavily on the nation and the world. Small Business in particular has been hard hit by the pandemic. Restaurants, bars, health and recreation clubs and many other businesses have suffered economic loss and closure.

Traditional ducted heating, ventilation, and air conditioning (HVAC) systems for commercial structures are inadequate in many ways for microbial mitigation. These systems rely on large ductwork with sub-par geometries, poor filtration, little or no air quality condition monitoring and significant inefficiencies. "Cold water slime", allergen, infiltration, dust buildup, noxious odors and stale air are all features of these outdated systems. As a result, conventional HVAC systems can actually be harmful in promoting the spread of microbes through the air.

Figure 1:
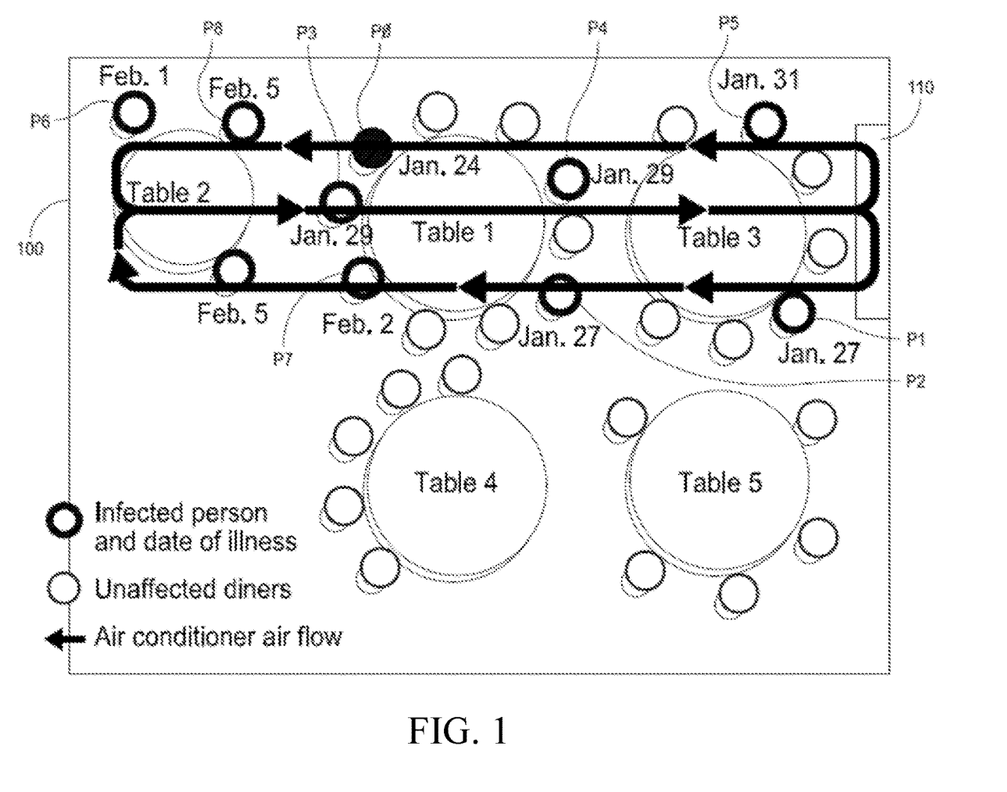
FIG. 1 is a diagram of a restaurant and an HVAC system associated with a study regarding viral infections.

FIG. 1 is an illustration from a real-world example study, (see, Lu J, Gu J, Li K, et al. COVID-19 Outbreak Associated with Air Conditioning in Restaurant, Guangzhou, China, 2020. Emerging Infectious Diseases. 2020; 26(7):1628-1631. doi:10.3201/eid2607.200764.) showing that traditional HVAC systems are not only unsuccessful at removing pathogens like SARS-CoV-2, they can enhance infection at various locations. FIG. 1 is a layout diagram of a restaurant 100 that includes patrons (indicated as smaller circles) sitting at Tables 1-5 (indicated as larger circles) and an HVAC unit 110 to condition air in the restaurant 100. The arrows indicate a flow of air from the HVAC unit 110. One of the patrons P0, patient zero, was infected with SARS-CoV-2 and several other patrons became infected (indicated by the bolded circle) after being exposed to patron P0 due to proximity to patron P0 and/or because of the circulation of HVAC generated air that moved the virus throughout the area. As shown, the following patrons became infected a period of time after dining; P1 and P2 three days; patrons P3 and P4 five days; P5 six days; P6 seven days; P7 eight days; P8 eleven days. As such, patrons located near areas where the HVAC was blowing on them directly became ill with COVID-19, whereas the other patrons outside of the air flow did not contract the virus.

Therefore, there is a need for an HVAC system that actively works to reduce microbial load that is easy to install, energy efficient, and cost effective in both new and specifically existing ducted systems. This need is economic, strategic and security based in nature. The present disclosure contemplates a feedback-driven system that is easy and rapid to implement and cost effective in new and existing structures.

Additionally, traditional ducted HVAC systems are energy inefficient. Moreover, International Building Code (IBC) fresh air requirements are traditionally based on calculated maximum occupancy, rather than space geometry or actual occupancy. HVAC in commercial structures constitutes over 32% of all energy use, with ventilation alone over 16%.

The present disclosure addresses issues presented by existing HVAC system options, including the challenges posed by airborne viral and microbial loads and the shortcomings of conventional air handling systems.

DETAILED DESCRIPTION

A disclosed system can include an air treatment system to control and distribute air throughout a condition space in a building or other structure. The air treatment system can include a handling unit having a variable-frequency drive (VFD) controlled high velocity air handler (HVAH). The air treatment system can be feedback-driven to provide active control over the movement of air within the conditioned space, which can be in response to detection of a contaminant or other substance in the conditioned space. Typical HVAH systems currently enjoy only a very limited application, primary in retrofitting historic homes for air conditioning (AC) where large ductwork or split system wall units are undesirable, unsightly, or would damage the historic resource and character of the structure. The present disclosure includes embodiments that incorporate an HVAH into an air treatment system to provide greater control over the air present in a conditioned space, including the option to immediately increase air flow and air removal at the detection of a contaminant or other substance (e.g., an excess amount of $CO_2$ or presence of a viral or microbial load).

The use of a HVAH is beneficial to the reduction in target materials in air, including viral loads. First, the HVAH helps to keep all of the internally-ducted flow in a turbulent state. This helps to eliminate any potential issues with dead and sessile non-flows of air in the handler that can result from laminar flow, which can be ideal places for microbes, dust and allergens, to reside in the system. Second, the HVAH allows the system to be unobtrusive, as they are smaller in size. An example is a traditional HVAC can require a 32" round duct, whereas a HVAH will require only an 11" round duct or less. This is particularly helpful on any potential retrofits of existing systems, as the new ductwork can be installed inside the existing ductwork. Third, the VFD-driven HVAH can be precision controlled to improve air quality through active feedback, but not introduce excessive amounts of unconditioned air, reducing energy consumption.

In some embodiments, the air treatment system incorporates an energy recovery ventilator (ERV), but controls it based on real-time air quality needs, not arbitrary fixed "maximum capacity" requirements. As a result, disclosed embodiments can greatly reduce energy consumption, such as by only introducing an amount of air needed for the specific real-time needs. The air flow can be driven by sensor feedback to a control system. In addition, the ERV can bypass the handling unit, such as to lessen a load on the handling unit as the fresh air will not have to be treated or filtered. The control system is configured to provide input to control the input of air from the handling unit and the ERV.

The disclosed treatment system can further include input based on geometric design for air flow. Internally, the ducting should maintain turbulent flow to eliminate dead spots which may be areas for stagnant air and microbe growth. A preferred ducting can be round or oval in nature (i.e. without sharp corners) and sufficiently insulated to prevent condensation and energy loss issues. In addition, the internal surfaces of the ductwork and machinery can be coated in antimicrobial materials including but not limited to copper, zinc, silver, chlorine, and titanium-dioxide containing materials. Externally, the supply and return ducting can be placed preferentially as to reduce overall mixing, but at the same time actively treat and remove microbial contaminants from the conditioned room. In some embodiments, the system can be implemented with ducting, supply outlets and return inlets that create "zones" within a conditioned space that are arranged to avoid significant mixing of the air between other zones. These zones can be further augmented by turbulent-to-laminar flow adapters such as tube-capillary and/or grid designs. Each return and supply port can be tuned for balanced air flow by proper valves and/or orifices of each port, which can be accomplished upon installation with volumetric air flow meters. The valves and orifices can be fixed or made variable for real-time process control through automated or manual processes. Proper balancing of air flow has been found to significantly impact the system performance. Balancing of the system can be accomplished by using pressure differential meters across a commercially available iris damper at both the feed and return locations, prior to the end effectors (i.e. nozzles).

The air treatment system can also employ a plurality of sensors positioned throughout the system to provide feedback to the control system and/or a managing user. The sensors can be configured to measure, for example, carbon dioxide, flow, pressure, particle/droplet (via photoelectric/ionization/optical/laser/other sensors), temperature, humidity, and/or pathogens. The sensor can include detection sensors configured to detect a target particle (e.g., a particular molecule, viral material, microbe, contaminant, dust, etc.). In some embodiments, the sensors can include an occupancy sensor configured to detect the presence of people in the room, such as through carbon dioxide, motion detection, infrared or other camera detection, such via image analysis.

According to disclosed embodiments, the treatment system is configured to adequately control the climate of the conditioned space, but effectively reduce the exposure to pathogens. The carbon dioxide sensors can provide occupancy information to the system. The greater the occupancy, the greater the measured $CO_2$ concentration above background will be, requiring more microbial mitigation and fresh air contribution. $CO_2$ sensors can be located in the open room, outdoors, supply and return ductwork. Flow sensors can be employed to control the amount of air supplied to the conditioned space, as well as sensing the amount of fresh air input/balancing from the ERV, meeting the intent of the IBC fresh air requirement while not wasting energy. In addition, flow sensors can be employed in the supply and return ports to balance the system to provide active control of air flow. Pressure sensors can be utilized to monitor HEPA MERV filter performance and function/condition monitoring of the handling unit. The particle/droplet sensors can be placed in the open room, supply and return ductwork as necessary. The temperature and humidity sensors can be placed in the conditioned space to provide feedback for a desired temperature set point. Humidity sensors, in particular, will allow the water content in the conditioned space to be tailored for microbial mitigation set points. Further, any pathogen sensors can be employed as desired. For example, biological sensors for viral or microbial materials such as anthrax, salmonella, influenza, SARS-CoV-2, can be positioned in conditioned spaces to detect the presence of pathogens. These sensors can be collocated with the particle sensors described above as required.

In some embodiments, the handling unit can include an ultraviolet C (UVC) sterilizer to treat air that moves through the handling unit. The UVC sterilizer employed can be an off the shelf unit that is capable of sterilizing the return air from the conditioned space and can function in a manner known in the art. The handling unit can additionally include an ionization unit. One example is a unit supplied by Atmosair®, which is reported to reduce coronaviruses by 99.92%. The ionization units create and introduce, via the handling unit, ionized particles that combine with and neutralize pathogens in the conditioned space.

The treatment system can be driven through a connected control unit (CU). The CU can be configured to receive real-time data from the sensor array, and make needed adjustments to the components of the handling unit, such as the VFD, ERV, and heating and cooling modules as needed to control the temperature, humidity, $CO_2$, and pathogen load of the conditioned space. In at least some embodiments, the control can be accomplished by an array of programmable logic controllers with digital and analog inputs and management software. The CU can be either locally or remotely monitored and controlled. In addition to the building owner/staff controlling the CU, remote monitoring services/firms can be employed to control, monitor, troubleshoot, collect data, and improve upon the operation/efficiency and function of the system. The remote monitoring services can notify building owners if any problems exist, upcoming needed maintenance, and also provide a record of the air quality that may prove useful for legal, scientific, and public health purposes. Further, the CU can be run in manual mode for testing, diagnostics, and simplified operation as needed.

Figure 2:
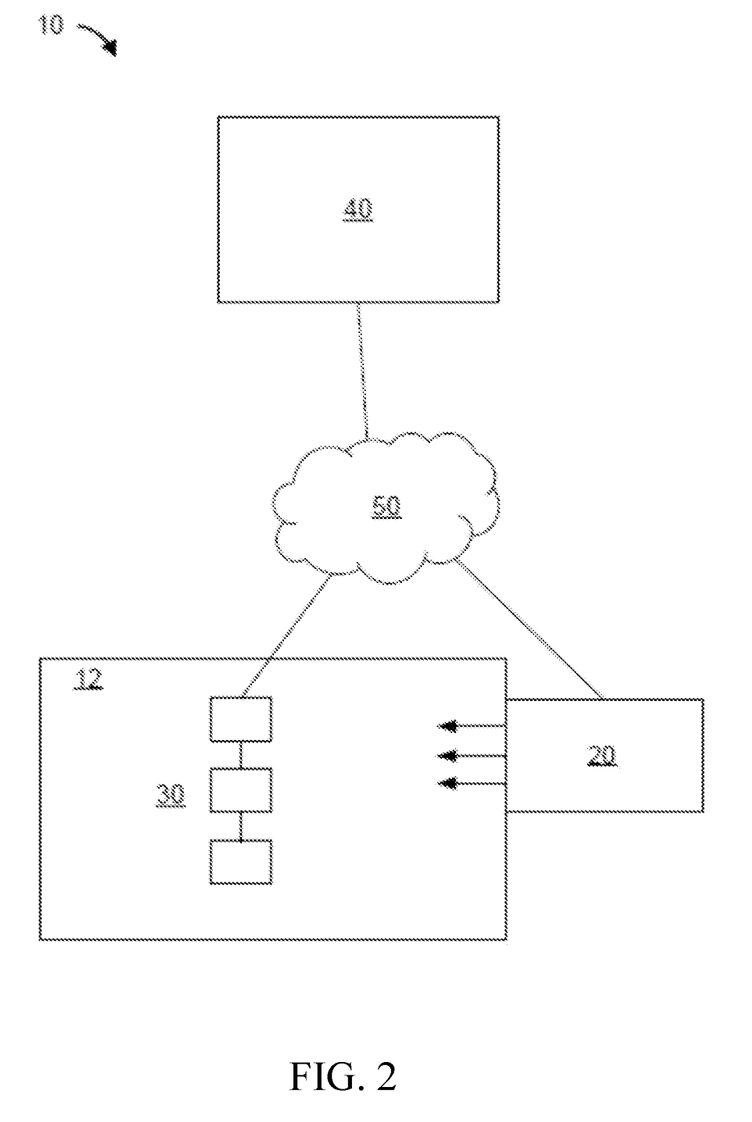
FIG. 2 is a block diagram of an exemplary feedback-driven air treatment system including a control system and other components connected to a network, according to a disclosed embodiment.

FIG. 2 is a diagram of an exemplary feedback-driven air treatment system 10 to handle air flow in and out of a conditioned space 12. The air treatment system 10, in an embodiment, includes a handling unit 20 to produce and handle air flow, a sensor array 30, a control system 40, and a network 50 to communicate between the components of the air treatment system 10.

The handling unit 20 can be a mechanical system, such as an HVAC system having a motor and fan for driving a volumetric air flow. The handling unit 20 can be connected to a plurality of air ducts 22 to supply and return air to and from the conditioned space 12. In an embodiment, the handling unit 20 and air ducts 22 include a HVAH system to produce high velocity air flow through the air ducts 22. The HVAH can, in an embodiment, maintain turbulent flow through the air ducts 22. The handling unit 20 can include air treatment components configured to condition air the passes through the unit. For example, the handling unit 20 can include heating/cooling, ionization, filtering, and/or sterilizing units, but are not limited thereto and can include other possible treatment features (e.g., humidifier, dehumidifier, etc.).

The sensor array 30 can include one or more sensors positioned at selected positions along an air flow path relative to the conditioned space 12, handling unit 20, and air ducts 22. The sensor array 30, in an embodiment, includes at least one sensor configured to generate a signal indicative of a measured parameter. The measured parameter can be a variable dependent on the type of sensor. For example, a carbon dioxide sensor can be configured to generate a signal indicative of a presence and/or amount of carbon dioxide detected at the sensor. In another example, a motion sensor can be configured to detect motion and generate a corresponding signal indicating the presence of an occupant in the room. In one embodiment, the sensor array 30 can include a general detection sensor configured to generate a signal indicative of the presence of a target material, such as a molecule, pathogen, viral load, microbe, etc. The sensor(s) in the sensor array 30 can be configured to deliver a generated signal to the control system 40.

The control system 40 can include a computing device configured to send and receive data to and from components of the air treatment system 10 and store and execute software instructions to perform a disclosed process. The control system 40 can include a single computing device or a plurality of connected computing devices. The control system 40 can be, for example, a laptop or desktop computer, mobile device, server, or the like. The control system 40 can include a display or other user interface component allowing interaction with a user, such as through a peripheral device. The control system 40 can be configured to receive signals from the sensor array 30 and provide instructions to the handling unit 20 to produce feedback-driven control over the air flow produced by the handling unit 20 and thus perform climate control of the air within the conditioned space 12.

The network 50 can be a communication device configured to connect the components of the air treatment system 10, such as the handling unit 20, sensor array 30, and control unit 40. The network 50 can be a wireless or wired communication device. The network 50 can be the cloud. In an exemplary embodiment, the network 50 is a wireless connection, such as one or more of WiFi, Bluetooth®, or the Internet. In other embodiments, the network 50 can include wired or integrated communication connections. The network 50 allows data communication between the components of the air treatment system 10.

Figure 3:
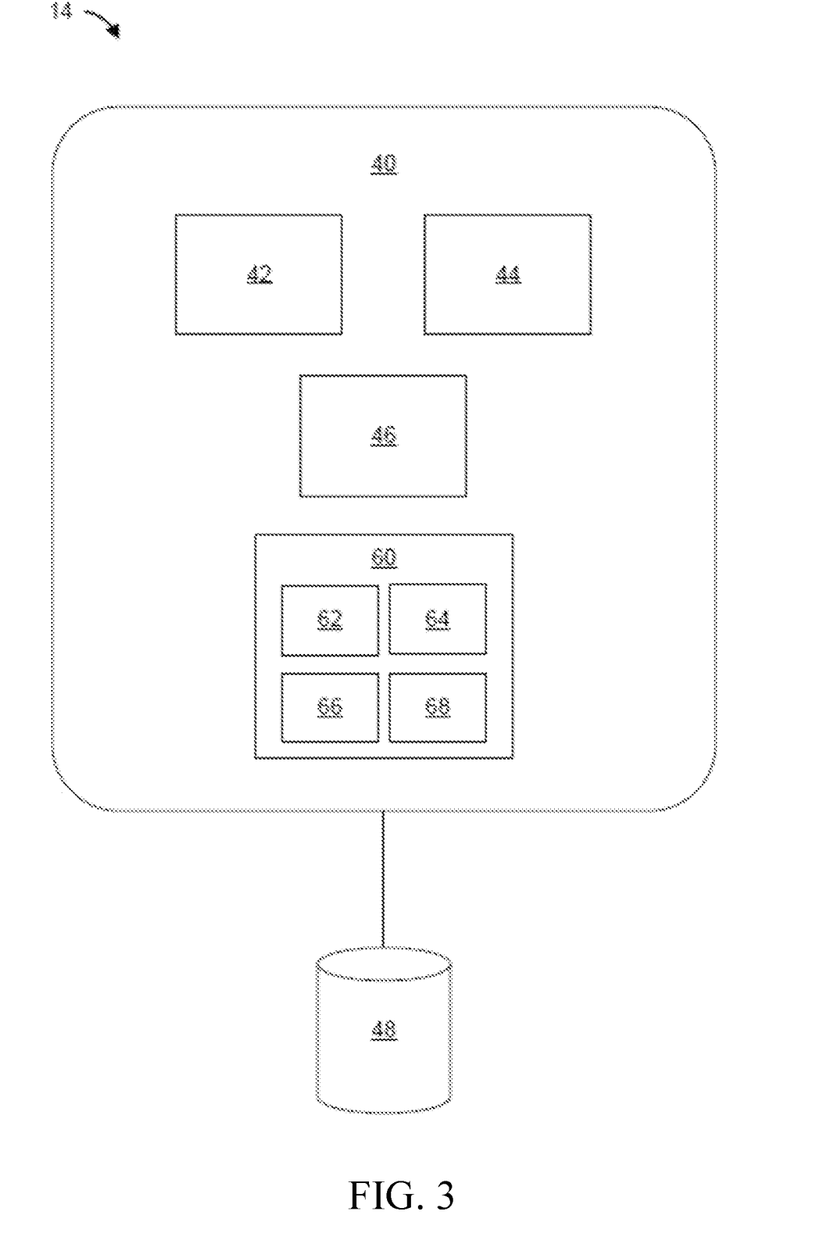
FIG. 3 is a block diagram of a computing device of a disclosed feedback-driven air treatment system.

FIG. 3 is a block diagram of an exemplary computing device 14, which, in an embodiment, includes the control system 40. The computing device 14 can include a processing unit 42, a memory unit 44, and one or more input/output device 46. The computing device 14 can, in some embodiments, be connected to a database 48, such as a data repository. While the computing device 14 is depicted and described as the control system 40, it can be representative of one or more integrated or constituent components of the handling unit 20, sensor array 30, network 50, or other component of the air treatment system 10.

The computing device 14 can be a general or specialized computing system or component configured to receive data and produce data signals to control a feature or component of the air treatment system 10, such as the handling unit 20. In an exemplary embodiment, the computing device 14 can include a plurality of engines or modules 60 configured to perform a disclosed process, such as through the execution of stored instructions. The modules 60 can include, in an exemplary embodiment, a sensing module 62, a rules module 64, an output module 66, and a learning module 68. The modules 60 can be implemented in hardware and/or software and can facilitate execution of one or more processes by the processing unit 42.

Figure 4:
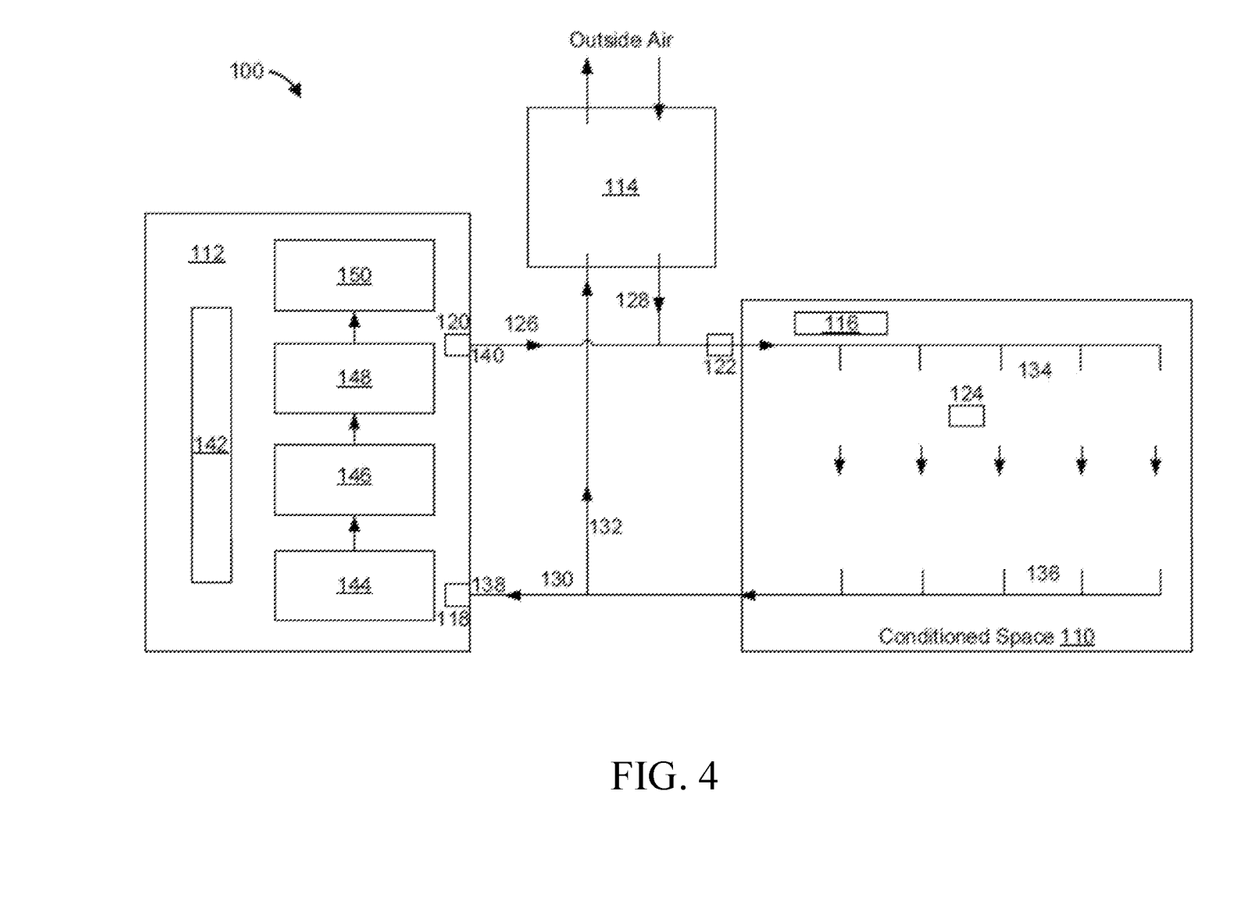
FIG. 4 is a block diagram of an air treatment system for a conditioned space, according to a disclosed embodiment.

FIG. 4 is a block diagram of an air treatment system 100. The air treatment system 100 can be an embodiment and/or exemplary implementation of the air treatment system 10. The air treatment system 100 can be configured to control air flow into and out of a conditioned space 110. The air treatment system 100 can include an air handling unit 112, an ERV system 114, a control system 116, a plurality of sensors 118, 120, 122, 124, a network of air ducts 126, 128, 130, and 132, one or more supply outlets 134, and one or more return inlets 136.

The air handling unit 112 can include an inlet 138 and an outlet 140 connected by a staged air treatment area. The air handling unit 112 can include a VFD controlled handler 142, such as a motor, fan, and power supply arrangement configured to produce high velocity air flow at the outlet 140. The air handling unit 112 can include a heating and cooling unit 144, a filtration unit 146, an ionization unit 148, and a sterilization unit 150. The heating and cooling unit 144 can be configured to increase and/or reduce a temperature of air passing through the air handling unit 112. The filtration unit 146 can be configured to remove contaminants, particles, and/or other target materials from the air flow. For example, the filtration unit 146 can be a HEPA MERV filter. The ionization unit 148 can be configured to apply a selected voltage to ionize or electrically charge air molecules as they pass through the air handling unit 112. The ionization unit 148 is configured to purify the air of contaminants, particles, and/or other target materials from the air flow. The sterilization unit 150 can be an additional stage for removing target contaminants, particles, and/or other materials, including viral and/or microbial loads from the air flow.

The network of air ducts 126, 128, 130, and 132 are configured to provide air to the conditioned space 110 from either or both of the air handling unit 112 and the ERV system 114 and return air from the conditioned space 110 to either or both of the air handling unit 112 and the ERV system 114. For example, in an embodiment, the air duct 126 supplies treated air from the air handling unit 112 to the one or more supply outlets 134 in the conditioned space 110. The air duct 128 provides air from the ERV system 114 to the one or more supply outlets 134. The air ducts 126 and 128 can meet at a junction and follow a combined path the to supply outlets 134 after the junction, although the ducts may be completely separate in some embodiments. The air duct 130 provides at least some of the air from the conditioned space 110 back to the air handling unit 112 through the one or more return inlets 136. The air duct 132 provides at least some of the air form the conditioned space to the ERV system 114 through the one or more return inlets 136. The air ducts 130 and 132 can follow a combined path from the one or more return inlets 136 to a junction and then split off to the air handling unit 112 and ERV system 114, respectively, although the ducts can be completely separate in some embodiments.

The air treatment system 100 is depicted as including four sensors 118, 120, 122, 124, but it should be understood that the any number of sensors and/or sensor types can be positioned anywhere within an area covered by the air treatment system 100. In an exemplary embodiment, the sensor 118 can be positioned at the inlet 138 and the sensor 120 can be positioned at the outlet 140 to provide a selected measurement before and after air is treated within the air handling unit 112 The sensor 122 can be positioned in the air duct 128 to measure a parameter associated with the air that enters through the ERV system 114. The sensor 124 can be positioned in the conditioned space 110 and be configured to detect the presence of a target material, for example. For instance, the sensor 124 can be a carbon dioxide sensor configured to generate a signal indicative of an amount of carbon dioxide near the sensor 124 in the conditioned space 110. Other examples of sensors that can be included in the air treatment system 100 include aerosol, biological, and humidity sensors.

The one or more sensors 118, 120, 122, 124 can be configured to generate and provide signals to the control system 116 indicative of a monitored and/or measured parameter associated with the air flow. For example, the air treatment system 100 can be set up such that the control system 116 receives feedback regarding the air flow through the ducts, the quality of the air in the conditioned space 110, the occupancy in the conditioned space 110, the effectiveness of any components of the air handling unit 112 or ERV system 114, or these systems as a whole, the flow rate of air at one or more of the supply outlets 134 and/or return inlets 136, the volumetric flow rate through the air handling unit 112 and/or ERV system 114, or the like.

Energy efficiency is obtained by the following. As mentioned, the ERV introduces fresh, unconditioned air. While the ERV can recover some of the energy from the exhausted air, they are not 100% efficient. Therefore, any fraction of introduced unconditioned air can need to be conditioned (i.e. raise or lower the temperature/humidity). In addition, current IBC commands that sufficient fresh air be supplied for the maximum capacity. For example, if a room has a capacity of 100 people, a fresh air supply is always required for 100, even if only 2 people are in the room at any period of time. The intent of the IBC is to eliminate stale air, i.e. air with odors, high $CO_2$, etc. Furthermore, due to the disclosed sensor feedback system, heating, cooling, humidity and more can be monitored and controlled more accurately, reducing excess overages and improving comfort, thus providing cost savings and efficiency all-around. Disclosed embodiments can include control methods in which sensor detection of a parameter indicative of an occupancy can lead to a corresponding air flow setting that is appropriate for the detected occupancy (e.g., more people, higher flow rate, and vice versa).

The control system 116 can be configured to receive a signal from one or more sensors 118, 120, 122, 124 and produce a control instruction to be provided to one or more of the components of the air treatment system 118. For example, the control system 116 can implement automated feedback control of the air handling unit 112 and/or ERV system 114 to increase and/or decrease a flow of air through the conditioned space 110. For example, if a parameter (e.g., carbon dioxide level, viral or microbial load, occupancy, etc. above a threshold) is detected by the sensor 124, the control system 116 provides a signal to the air handling unit 112 and/or the ERV system 114 to increase air flow through the air ducts 126, 128 to quickly and efficiently replace the air in the conditioned space 110 and direct the replaced air to pass through the treatment stages of the air handling unit 112.

In one example, the control system 116 can monitor one or more of the sensors 118, 120, 122, 124 for a pressure change. If the control system 116 detects a pressure change (e.g., in the filters), the control system 116 can instruct the air handling unit 112 and/or ERV system 114 to introduce additional air flow to compensate. In some embodiments, real-time pressure monitoring of the air ducts, inlets, and outlets is provided, such as to help tune the performance of the air handling unit 112 and/or ERV system 114, as different ratios of air sources (air handling unit vs. ERV system) can perform differently and can be detected and/or adjusted based on pressure and/or flow measurements.

In another example, the control system 116 can provide feedback to a user, such as a building or property manager, through a user interface. The control system 116 can be further configured to receive input through the user interface to produce a control instruction for one or more of the components of the air treatment system 100.

According to disclosed embodiments, the air treatment system 100 can implement high velocity air flow to quickly and efficiently move air through the conditioned space 110 when needed and/or desired, as well as to more efficiently control air flow. The air treatment system 110 can use small, round air ducting that is amenable to consistent turbulent flow. Such systems are particularly applicable to retrofit applications, as the smaller ducting may be fit within larger, existing ducting with adapter plates and supports to effectively position the high velocity ducts and seal off unused areas of the older ductwork. The high velocity system can include features to modify the air flow when it reaches the conditioned space 110. For example, the supply outlets 134, according to some embodiments, can be turbulent-to-laminar flow adapters.

Figure 5:
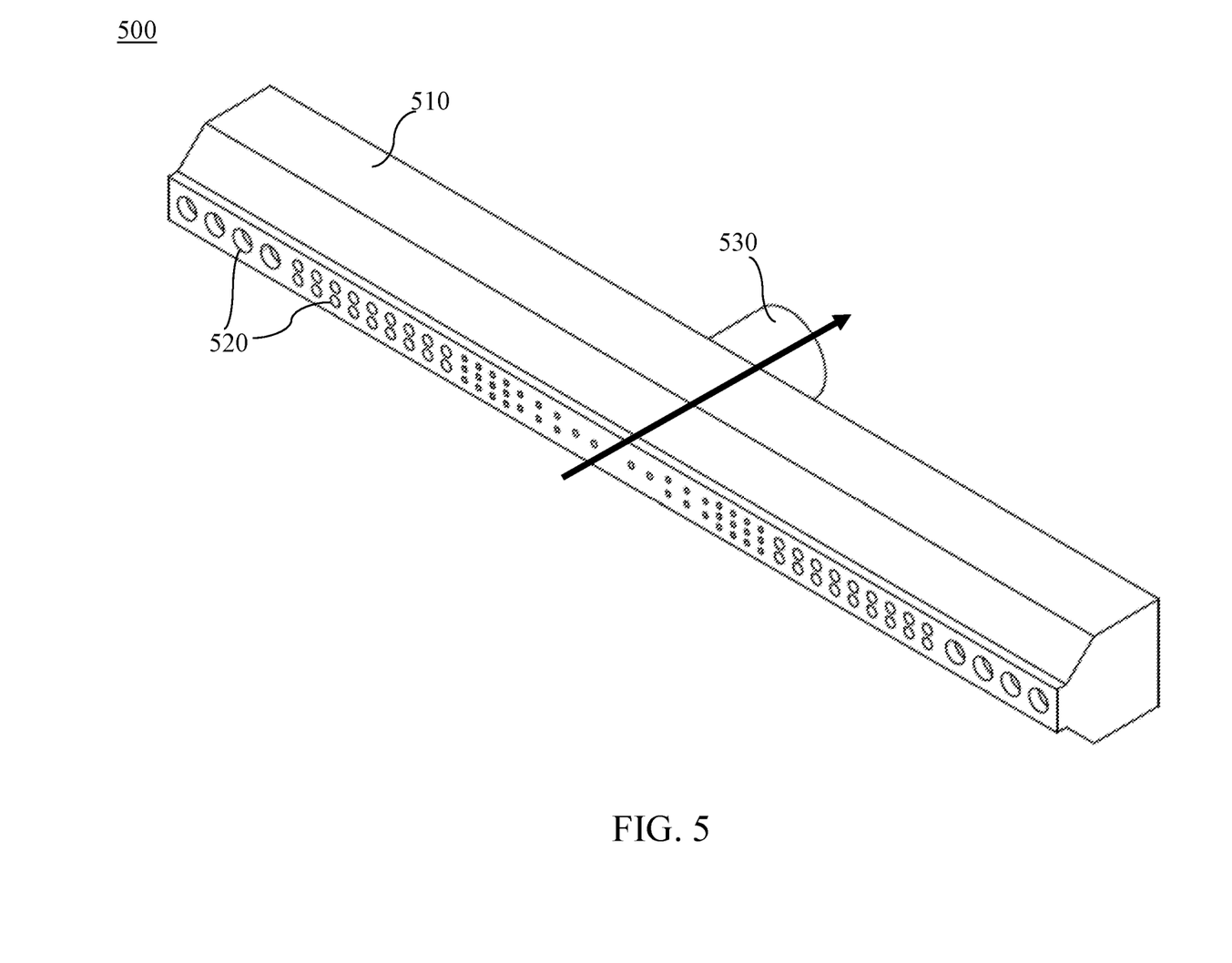
FIG. 5 is an illustration of an exemplary air inlet according to an embodiment.

FIG. 5 shows a return inlet 500 according to an embodiment of the present invention. The dark arrow shows the direction of air flow. As shown, the return inlet 500 can include a body or air box 510, a plurality of openings 520 on one surface to allow air to enter the air box 510, and an air outlet 530. The air box 510 is empty to allow the air input through the openings 520 to travel through the openings 520, through the air box 510, and through the air outlet 530 to an adjoining return air duct (not shown). The plurality of openings 520 includes openings with several size diameters. As shown, openings 520 with larger diameters are located toward to two ends of the return inlet 500 with diameters of openings being reduced as the openings are located closer to the center of the return inlet 500. This configuration allows the air pressure to be balanced over the whole length of the return inlet 500 to even out the air flow. Balancing of the return allows for equal flows across the entire return inlet, allowing for more linear flows from the feed to reduce mixing and reducing microbial loads.

Figure 6:
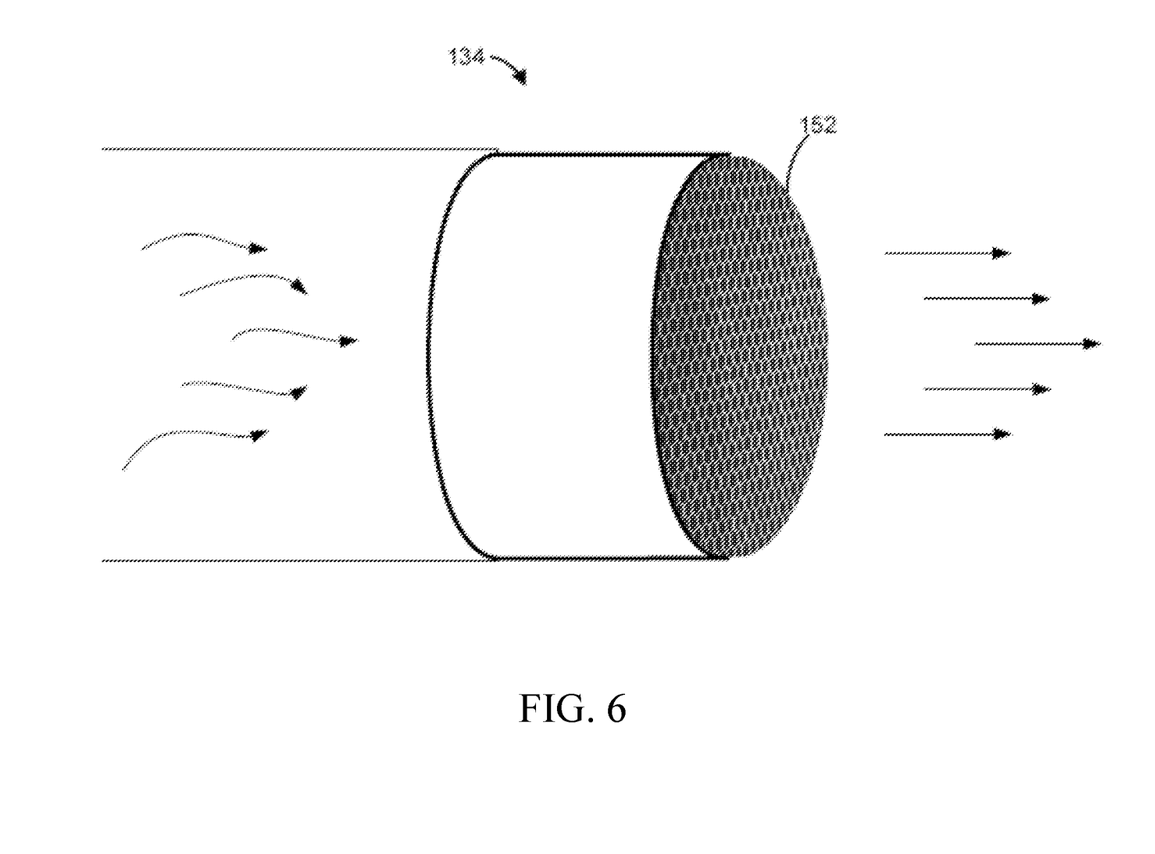
FIG. 6 is an illustration of an exemplary air outlet according to an embodiment.

FIGS. 6-9 show exemplary embodiments of supply outlets. FIG. 6 includes an exemplary embodiment of a supply outlet 134. The supply outlet 134 includes an adapter 152 configured to convert a substantially turbulent air flow inside of an air duct into a substantially laminar flow into the conditioned space 110. The adapter 152 thereby allows more precise control over the flow of air within the conditioned space 110 while also utilizing the high velocity system described herein. In an exemplary embodiment, the adapter 152 includes a honeycomb or multiple-orifice configuration that creates a plurality of outlets substantially parallel to each other.

The adapter 152 can be provided at each of the supply outlets 134, such that geometric considerations can be used when implementing the air treatment system 110 for a particular conditioned space 110. In some embodiments, the supply outlets 134 and return inlets 136 can be particularly arranged to create a plurality of zones 154 within the conditioned space 112. The laminar flow produced by the supply outlets 134 serves an advantageous purpose when combined with the use of the zones 154. In particular, the zones 154 can be arranged such that minimal mixing occurs at the boundaries of the zones 154. As a result, unwanted contaminants can be quickly and efficiently removed from the conditioned space 112 without moving the contaminants throughout a large portion of the space, potentially affecting and/or infecting multiple occupants in the space. For example, if a particular viral contaminant is detected in the space, it can be quickly evacuated by passing through only one zone and preventing contact with individuals in other zones.

Figure 7:
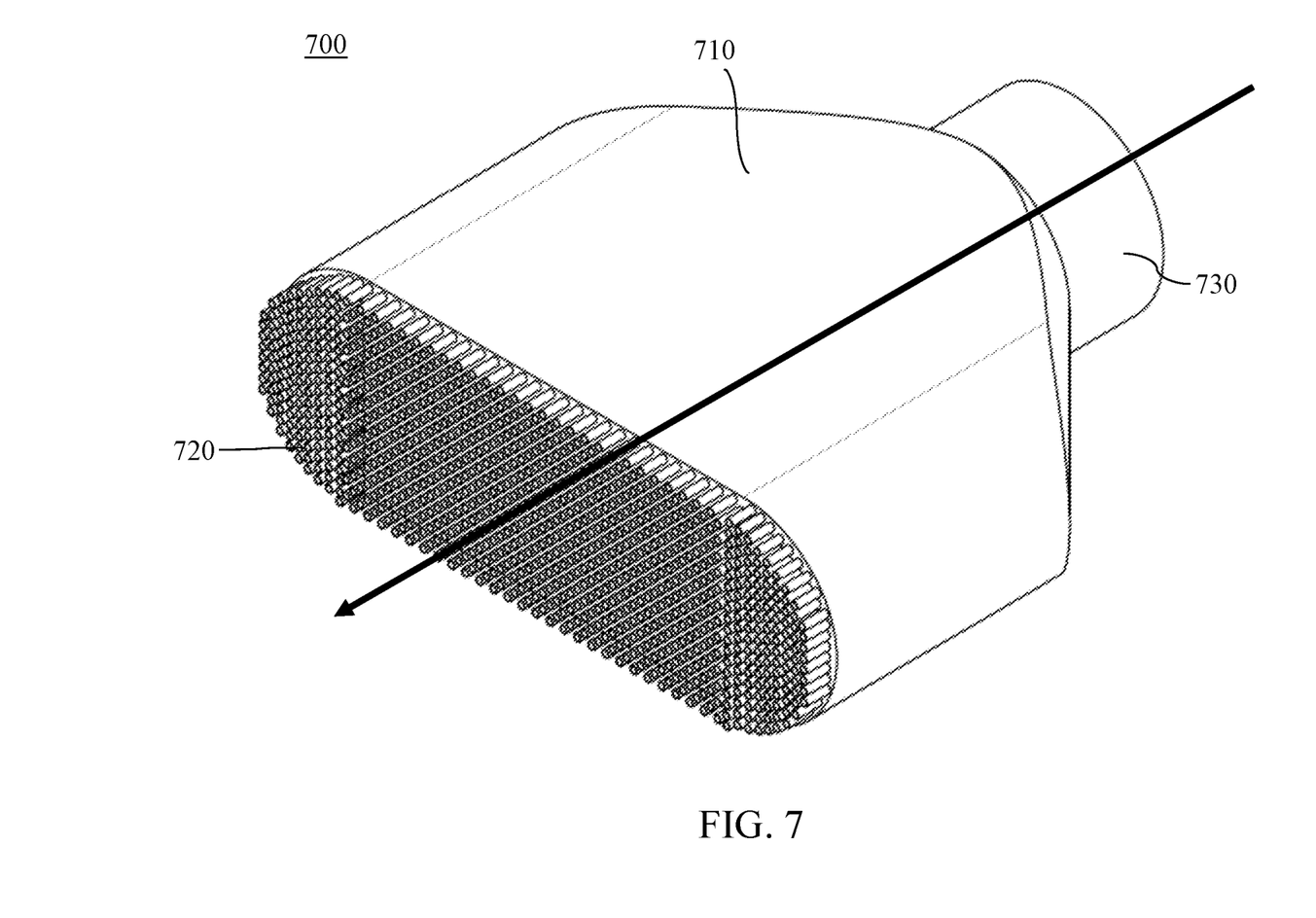
FIG. 7 is an illustration of an exemplary air outlet according to another embodiment.

FIG. 7 shows another exemplary embodiment of a supply outlet 700. The supply outlet 700 includes an adapter or plurality of outlets 720 configured to convert a substantially turbulent air flow inside of an air duct (not shown) connected to the air inlet 730 and the air box 710 into a substantially laminar flow into the conditioned space 110. The dark arrow shows the direction of air flow. The adapter 700 allows more precise control over the flow of air within the conditioned space 110 while also utilizing the high velocity system described herein. As shown, the adapter 700 includes a multiple-orifice configuration that creates an array of a plurality of outlets 720 that are substantially parallel to each other. Air travels from the air inlet 730 into the air box 710 and only through the air outlets 720. Air is blocked from traveling out from the air box 710 between the outlets 720. As shown, the air outlets 720 each protrude from a surface of the air box 710. Although not shown, the air outlets also protrude into the air box 710.

Figure 8A:
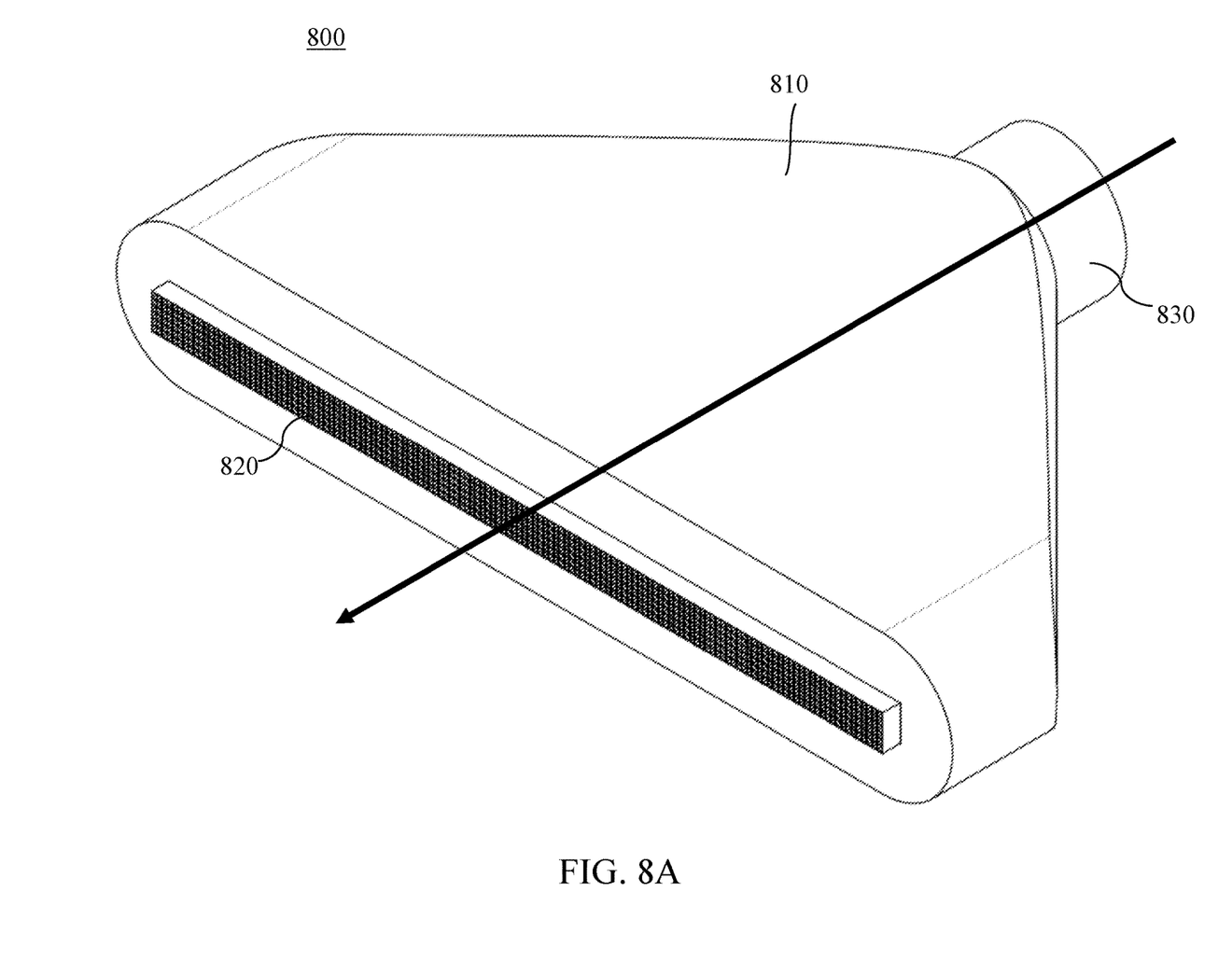
FIGS. 8A and 8B are illustrations of an exemplary air outlet according to another embodiment.
Figure 8B:
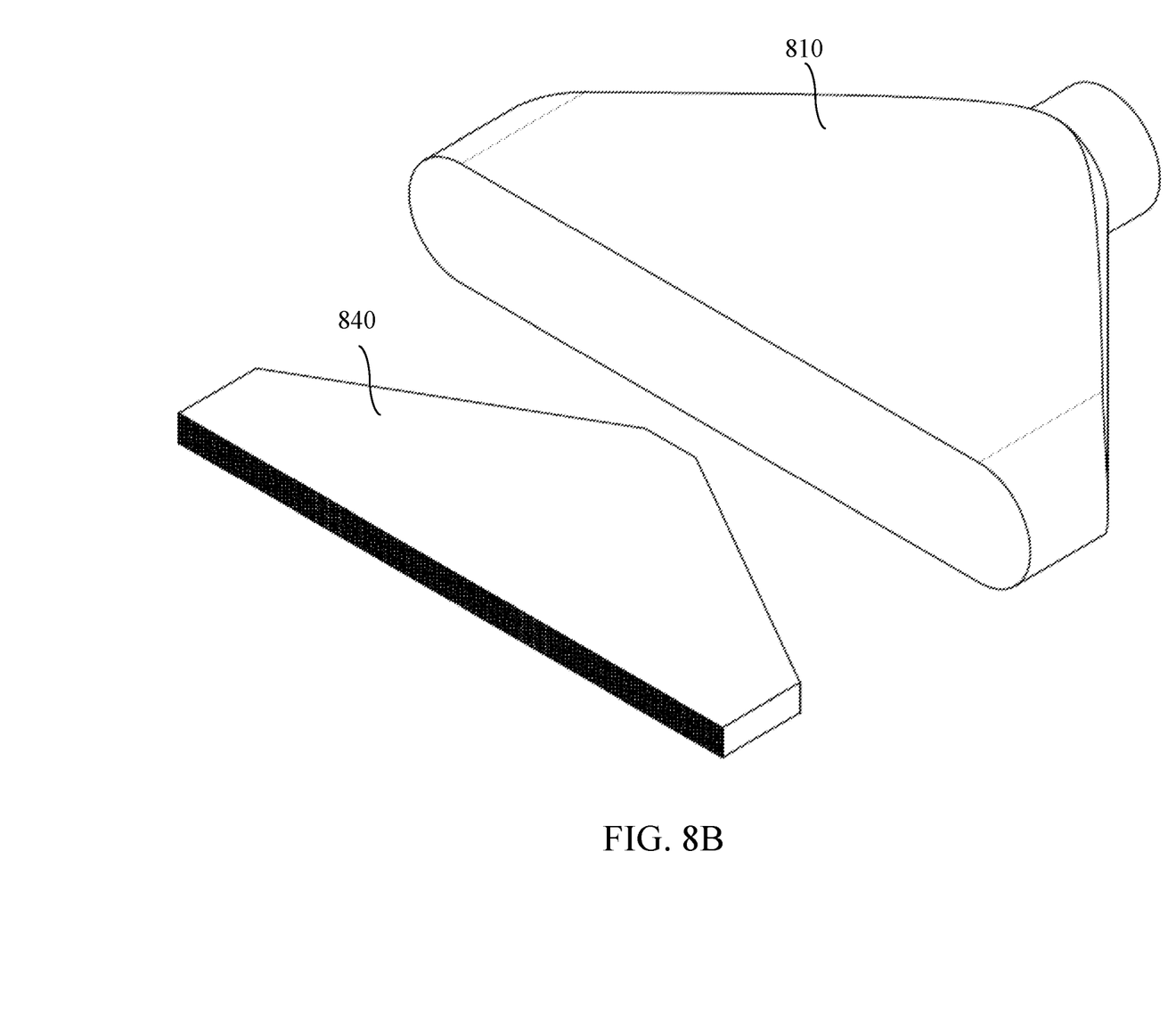

FIGS. 8A and 8B show another exemplary embodiment of a supply outlet 800. The supply outlet 800 includes an adapter or plurality of outlets 820 configured to convert a substantially turbulent air flow inside of an air duct (not shown) connected to the air inlet 830 and the air box 810 into a substantially laminar flow into the conditioned space 110. The dark arrow shows the direction of air flow. The adapter 800 allows more precise control over the flow of air within the conditioned space 110 while also utilizing the high velocity system described herein. As shown, the adapter 800 includes a multiple-orifice configuration that creates an array of a plurality of outlets 820 that are substantially parallel to each other. Air travels from the air inlet 830 into the air box 810 and only through the air outlets 820. In this configuration, the air outlets 820 are define by passages through a laminated corrugated sheet structure 840 shown in FIG. 8B. The laminated corrugated sheet structure 840 that define the outlets 820 can be similar to corrugated plastic such as coroboard or coroplast.

Figure 9:
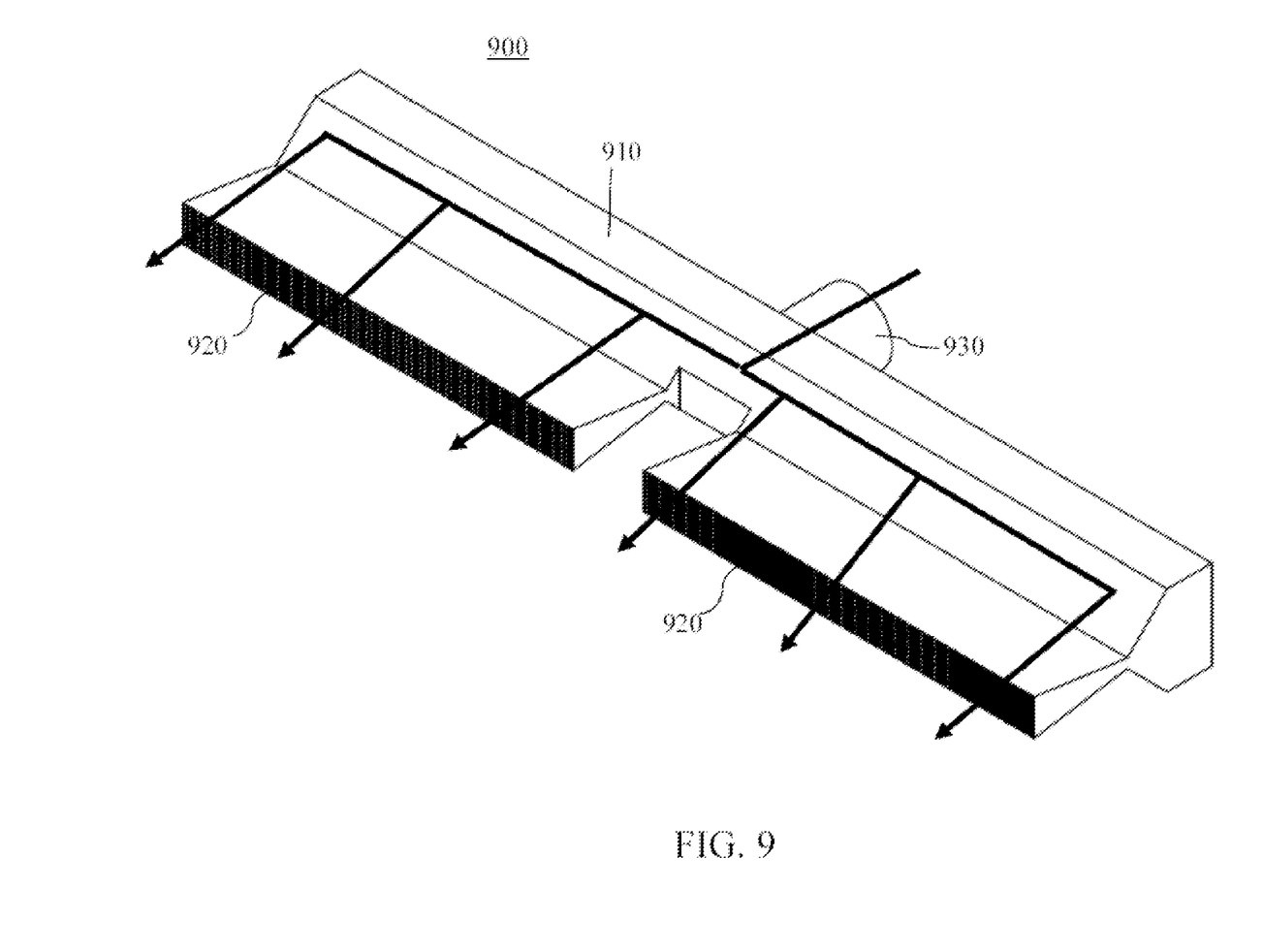
FIG. 9 is an illustration of an exemplary air outlet according to another embodiment.

FIG. 9 shows another exemplary embodiment of a supply outlet 900. The supply outlet 900 includes an adapter or plurality of outlets 920 configured to convert a substantially turbulent air flow inside of an air duct (not shown) connected to the air inlet 930 and the air box 910 into a substantially laminar flow into the conditioned space 110. The dark arrow shows the direction of air flow. The outlets 920 are constructed of laminated corrugated sheet structure similar to corrugated plastic described with respect to the supply outlet 800. Here, the air box 910 is configured to block any air from exiting the central portion of the air box 910 in a region where not air outlets are provided. Thus, the air flow through the air box 910 is directed toward each end. This configuration avoids effects of the air in the central portion just inside the air box 910 from the air inlet 930. As shown, the portion of the air box 910 including the outlets 920 is conical or divergent shaped to spread the air out as it flows from the air box 910 toward the outlets 920.

Figure 10:
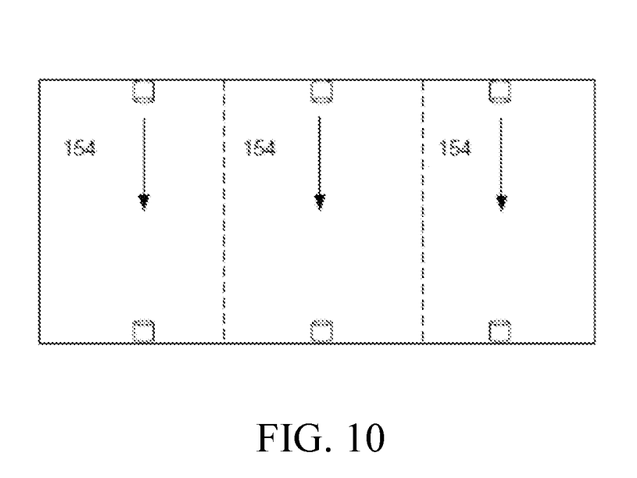
FIG. 10 is a diagram of a building structure having multiple air flow zones, according to an embodiment.
Figure 11:
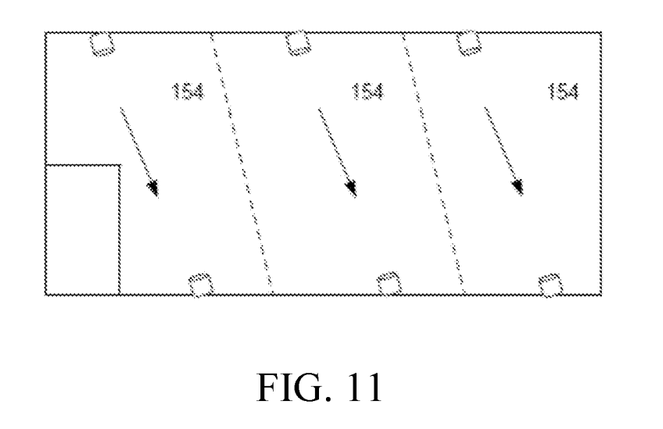
FIG. 11 is another diagram of a building structure having multiple air flow zones, according to an embodiment.
Figure 12:
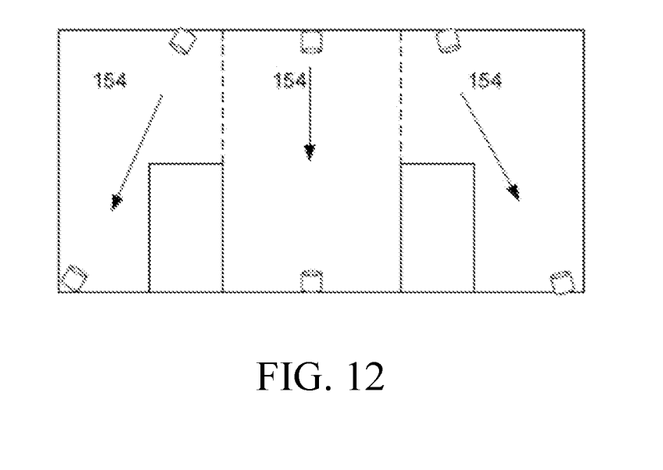
FIG. 12 is another diagram of a building structure having multiple air flow zones, according to an embodiment.

FIGS. 10-12 provide examples of various zones 154 that can be provided depending on the geometric configuration of the conditioned space 112. In FIG. 10, the zones are arranged in a parallel configuration and the supply outlets 134 are arranged to provide parallel flow perpendicular to the space. In FIG. 11, a wall obstruction changes the shape of the conditioned space, and the zones 154 are angled with respect to the overall building structure, while maintaining a parallel configuration. In FIG. 12, multiple wall obstructions produce zones 154 and flow configurations from supply outlets 134 that are angled with respect to each other. The disclosed features may be implemented in the form of a software program for modeling air flow through a conditioned space and generating optical geometric zones for efficient air flow through the entire space.

The disclosed embodiments provide an air treatment system that can be employed in a building structure or other conditioned air environment. The air treatment system can be particularly applicable to commercial and other non-residential spaces in which larger gatherings of people are possible and thus viral transmission is more likely and widespread. The disclosed embodiments include air handling features to produce high velocity flow to quickly and efficiently condition and replace air within an occupied space. The disclosed feedback system enables the air treatment system to monitor and detect parameters and conditions within an air flow path and control components as needed. For instance, the disclosed system can detect high occupancy and increase a rate of air replacement to avoid allowing potentially contaminated air to linger among occupants. In another example, detection of a target material, such as a viral load or pathogen, can cause the system to evacuate the air, which can be targeted to specific zone within the space, and introduce fresh and/or treated air to help inhibit the spread of virus and disease. The disclosed embodiments can further include components and configurations, such as laminar flow adapters, to help prevent excessive mixing of air flows to thereby minimize an area that can be exposed to an airborne pathogen or other material. The disclosed embodiments thus provide an air treatment system that addresses the shortcomings of current systems, including those associated with energy efficiency and uncontrolled or exacerbated spread of airborne materials.

Although embodiments have been described in terms of exemplary features, they are not limited thereto. Rather, the appended claims should be construed broadly, to include other variants and embodiments, which may be made by those skilled in the art without departing from the scope and range of equivalents.

What is claimed is:

1. An air treatment system, comprising:
   an air handling unit to direct air into a building structure;
   a sensor to detect the presence of a target material and produce a signal indicative of the detection of a target material greater than a threshold amount;
   a control system to control the air handling unit based on the signal from the sensor; and
   an air supply outlet including an air box connected to the air handling unit and an adapter in the air box and including multiple-orifices that create an array of a plurality of outlets that are substantially parallel to each other configured to convert a substantially turbulent air flow inside of an air duct into a substantially laminar flow into a conditioned space, wherein
   the plurality of air outlets are defined by an array of a plurality of passages through a honeycomb structure that are substantially parallel to each other.

2. The air flow system of claim 1, wherein
   the air handling unit includes a network of air ducts, and
   the air handling unit provides air flow in a turbulent state through the plurality of air ducts.

3. The air flow system of claim 2, wherein the air handling unit includes a plurality of duct outlets at a plurality of zones within the building structure.

4. The air flow system of claim 1, wherein the air handling unit includes a HEPA filter and a UVC sterilizer.

5. The air flow system of claim 1, wherein the air handling unit includes an ionization unit.

6. The air flow system of claim 1, wherein the control system and the air handling unit are remotely connected to each other via a network.

7. An air treatment system, comprising:
   an air handler to direct air into a building structure;
   an energy recovery ventilator to direct fresh air into the building structure and expel air from the building structure;
   a network of air ducts fluidly connecting the air handler and the energy recovery ventilator to a conditioned space within the building structure, wherein
   the network of air ducts supply air from the air handler and the energy recovery ventilator in a turbulent state to a plurality of supply outlets at the conditioned space,
   a plurality of sensors to measure a parameter associated with an air flow path defined by the air handler, the energy recovery ventilator; the network of air ducts, and the conditioned space,
   a control system to control the air handler and the energy recovery ventilator based on the parameter, and
   the plurality of supply outlets are an array of a plurality of passages through a honeycomb structure that are substantially parallel to each other.

8. The air treatment system of claim 7, wherein the network of air ducts are located within a plurality of pre-existing, larger air ducts in the building structure.

9. The air treatment system of claim 7, wherein the plurality of supply outlets include turbulent-to-laminar flow adapters.

10. The air treatment system of claim 9, wherein the conditioned space is divided into a plurality of zones with a supply outlet per zone.

11. The air treatment system of claim 10, further comprising a plurality of return inlets, wherein each of the plurality of zones includes a return inlet corresponding to a supply outlet.

12. The air treatment system of claim 10, wherein the plurality of zones are defined based on geometry of the conditioned space.

13. The air treatment system of claim 7, wherein the control system controls a ratio of air supplied by the air handler to air supplied by the energy recovery ventilator.

14. The air treatment system of claim 7, wherein the plurality of sensors includes a carbon dioxide sensor.

15. The air treatment system of claim 7, wherein the plurality of sensors includes a detection sensor that generates a signal indicative of the presence of a target material.

16. The air treatment system of claim 15, wherein the target material is one of a molecule, a pathogen, a viral load, and a microbe.

17. The air treatment system of claim 15, wherein the target material is COVID-19/SARS-COV-2.

18. A method, comprising:
    generating, by a sensor placed in a conditioned space, a signal based on detection of an amount of carbon dioxide in the conditioned space;
    receiving, by a control system, the signal from the sensor;
    determining, by the control system, an air flow setting based on the amount of carbon dioxide;
    providing, by the control system, a control signal to an air handler or an energy recovery system based on the air flow setting; and
    forcing air from the air handler to multiple-orifices that create an array of a plurality of outlets that are substantially parallel to each other and configured to convert a substantially turbulent air flow inside of an air duct into a substantially laminar flow into a conditioned space, wherein
    the plurality of air outlets are defined by an array of a plurality of passages through a honeycomb structure that are substantially parallel to each other.

19. The method of claim 18, wherein the amount of carbon dioxide is indicative of an occupancy of the conditioned space and the control signal indicates a target volumetric flow rate based on the occupancy.

20. The method of claim 18, wherein the control signal indicates an immediate increase in volumetric flow rate to replace the air in the conditioned space.

* * * * *